United States Patent
Esthappan et al.

(10) Patent No.: US 9,248,310 B2
(45) Date of Patent: Feb. 2, 2016

(54) GYNECOLOGICAL BRACHYTHERAPY APPLICATOR FOR USE IN MR-GUIDED INTRACAVITARY BRACHYTHERAPY

(75) Inventors: Jacqueline Esthappan, St. Louis, MO (US); Perry Grigsby, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 44 days.

(21) Appl. No.: 13/598,026

(22) Filed: Aug. 29, 2012

(65) Prior Publication Data

US 2013/0053682 A1 Feb. 28, 2013

Related U.S. Application Data

(60) Provisional application No. 61/529,574, filed on Aug. 31, 2011.

(51) Int. Cl.
*A61N 5/00* (2006.01)
*A61N 5/10* (2006.01)
*A61B 5/055* (2006.01)

(52) U.S. Cl.
CPC .............. *A61N 5/10* (2013.01); *A61N 5/1016* (2013.01); *A61B 5/055* (2013.01); *A61N 2005/1055* (2013.01)

(58) Field of Classification Search
USPC .......................................................... 600/6
See application file for complete search history.

(56) References Cited

U.S. PATENT DOCUMENTS

| 3,807,386 | A | * | 4/1974 | Rocoplan et al. | 600/6 |
| 5,012,357 | A | | 4/1991 | Schoeppel et al. | |
| 5,713,828 | A | * | 2/1998 | Coniglione | 600/7 |
| 6,390,968 | B1 | | 5/2002 | Harmon | |
| 7,666,130 | B2 | | 2/2010 | Mick | |
| 7,744,521 | B2 | | 6/2010 | Francescatti et al. | |
| 7,918,778 | B2 | | 4/2011 | Lim et al. | |
| 2008/0167514 | A1 | * | 7/2008 | Lim et al. | 600/6 |
| 2009/0216062 | A1 | * | 8/2009 | Axelrod et al. | 600/5 |
| 2010/0048978 | A1 | * | 2/2010 | Sing et al. | 600/6 |
| 2010/0145132 | A1 | * | 6/2010 | Isham | 600/7 |

OTHER PUBLICATIONS

Perez-Calatayud J, Kuipers F, Ballester F, et al. Exclusive MRI-based tandem and colpostats reconstruction in gynaecological brachytherapy treatment planning. Radiother Oncol 2009;91:181-186.

(Continued)

*Primary Examiner* — Long V Le
*Assistant Examiner* — Kevin Pontius
(74) *Attorney, Agent, or Firm* — Armstrong Teasdale LLP

(57) ABSTRACT

A gynecological brachytherapy applicator for use in delivering a radiation dose to a tumor affecting a uterus and a cervix of a patient is described herein. The applicator includes an intrauterine tandem that includes a base portion and a tip portion extending outwardly from the base portion. The tip portion is configured to be inserted within the uterus to facilitate delivering a radiation dose to an area including the uterus and the cervix. The tandem is configured to reduce metal artifacts in MR images of the tandem within the patient to facilitate improving visualization and localization of the tandem in the MR images during MR-guided intracavitary brachytherapy.

17 Claims, 15 Drawing Sheets

(56) References Cited

OTHER PUBLICATIONS

Haack S, Nielsen SK, Lindegaard JC, et al. Applicator reconstruction in MRI 3D image-based dose planning of brachytherapy for cervical cancer. Radiother Oncol 2009;91:187-193.

Kim Y, Muruganandham M, Modrick JM, et al. Evaluation of Artifacts and Distortions of Titanium Applicators on 3.0- Tesla MRI: Feasibility of Titanium Applicators in MRI-Guided Brachytherapy for Gynecological Cancer. Int J Radiation Oncol Biol Phys 2011;80:947-955.

Varian Medical Systems "Varian BrachyTherapy Applicators and Accessories"; Brochure 2011.

* cited by examiner

GYNECOLOGICAL BRACHYTHERAPY APPLICATOR FOR USE IN MR-GUIDED INTRACAVITARY BRACHYTHERAPY

CROSS REFERENCE TO RELATED APPLICATION

This application claims priority to U.S. provisional application No. 61/529,574 filed Aug. 31, 2011, which is incorporated herein in its entirety.

BACKGROUND

Tandem and colpostat, and tandem and ring applicators are each used for treating cervical and uterine cancer with high-dose-rate (HDR) brachytherapy, a process for delivering high-intensity radiation directly into tumor sites. The tandem and colpostats/ring are placed near the tumor and radiation therapy is given through the applicator by placing a radioactive source at multiple positions inside the hollow portions of the applicator. Worldwide, each year more than 600,000 women develop some form of gynecological cancer.

At least some known brachytherapy techniques use image guided brachytherapy (IGBT) that includes cross sectional image data to create 3D models of the anatomical structures. For example, known image guided brachytherapy include computed tomography (CT) and magnetic resonance imaging (MRI) systems. These systems are used for checking applicator placement and brachytherapy dose planning. The precise placement of the applicator is important for the radiotherapy to be optimally targeted to the tumor.

Imaging for gynecological brachytherapy is slowly evolving from planar x-rays to CT to MR volumetric imaging for improved visualization of the patient normal anatomy and disease. At least some known tandem and colpostat/ring applicators are made of titanium so that that they are stable and do not bend, deform, or move within the patient. When these titanium tandems are used with MRI, artifacts are created which cause a distortion of the boundaries of the applicator, which in turn hinders the ability to define the exact localization of the tandem in proximity to the tumor and in turn to optimally target the radiotherapy to the tumor.

BRIEF DESCRIPTION

The subject matter disclosed herein relates generally to gynecological brachytherapy applicators and, more specifically, to gynecological brachytherapy applicators for use in MRI-guided intracavitary brachytherapy.

In one aspect, a gynecological brachytherapy applicator for use in delivering a radiation dose to a tumor affecting a uterus and a cervix of a patient is provided. The applicator includes an intrauterine tandem that includes a base portion and a tip portion extending outwardly from the base portion. The tip portion is configured to be inserted into the uterus to facilitate delivering a radiation dose to an area including the uterus and the cervix. A sheath (may also be referred to as a sleeve herein) is removably coupled to the tandem. The sheath includes an inner surface that defines a cavity extending between a first open end and a second closed end. The tip portion is oriented within the cavity such that the sheath inner surface substantially circumscribes an outer surface of the tip portion. The sheath includes a plastic material that is configured to reduce metal artifacts in MR images of the tandem within the patient to facilitate improving visualization and localization of the tip portion in the MR images during MR-guided intracavitary brachytherapy.

In another aspect, a sheath for use with a gynecological brachytherapy applicator is provided. The applicator includes an intrauterine tandem that includes a base portion and a tip portion extending outwardly from the base portion. The sheath includes a sidewall that includes an inner surface that defines a cavity extending between a first open end and a second closed end. The cavity is sized to receive the tandem tip portion therein such that the inner surface substantially encapsulates the tip portion. The sheath is adapted to be removably coupled to the tip portion to facilitate improving visualization and localization of the tip portion in MR images of the tandem within the patient during MR-guided intracavitary brachytherapy.

In yet another aspect, a gynecological brachytherapy applicator for use in delivering a radiation dose to a tumor affecting a uterus and a cervix of a patient is provided. The applicator includes an intrauterine tandem that includes a base portion and a tip portion extending outwardly from the base portion. The tip portion is configured to be inserted within the uterus to facilitate delivering a radiation dose to an area including the uterus and the cervix. The tandem also includes a sidewall extending between a radially inner surface and a radially outer surface. The sidewall includes a substrate material that includes a surface region. At least one imaging layer is deposited across the surface region to at least partially define the tip portion outer surface. The at least one imaging layer is configured to reduce metal artifacts in MR images of the tip portion within the patient to facilitate improving visualization and localization of the tip portion in MR images of the tandem within the patient during MR-guided intracavitary brachytherapy.

DETAILED DESCRIPTION

The exemplary methods and systems described herein provide an applicator that is configured to reduce the metal artifact in MR images. More specifically, the brachytherapy applicator described herein includes a titanium tandem, and a plastic sheath that encapsulates the tandem and reduces metal artifacts in MR images to facilitate improving tandem visualization and localization for MR-guided intracavitary brachytherapy planning. In addition, the applicator is configured to reduce distortions in MR images such that the applicator displayed in the MRI has a geometry that is approximately equal to the actual geometry of the applicator. Aspects of the disclosure allow for improved MRI localization of the applicator relative to the tumor which in turn allow for the radiotherapy to be more optimally targeted to the tumor. The tandem applicator described herein is MR compatible and MR-distortion free, and rigid enough that it does not deform or move within the patient. These characteristics allow for localization of the applicator relative to the tumor which in turn allow for the radiotherapy to be more optimally targeted to the tumor.

The embodiments described herein include: (1) a plastic, disposable, thin-walled sleeve of known geometry that can be slid over the tip of the titanium tandem and locked in place to reduce the distortion in MR images and (2) a thinly plastic-coated titanium tandem. Thus, these systems combine the rigid structure, light weight, and small diameter of titanium with the distortion-reducing nature of plastic.

Figure 1:
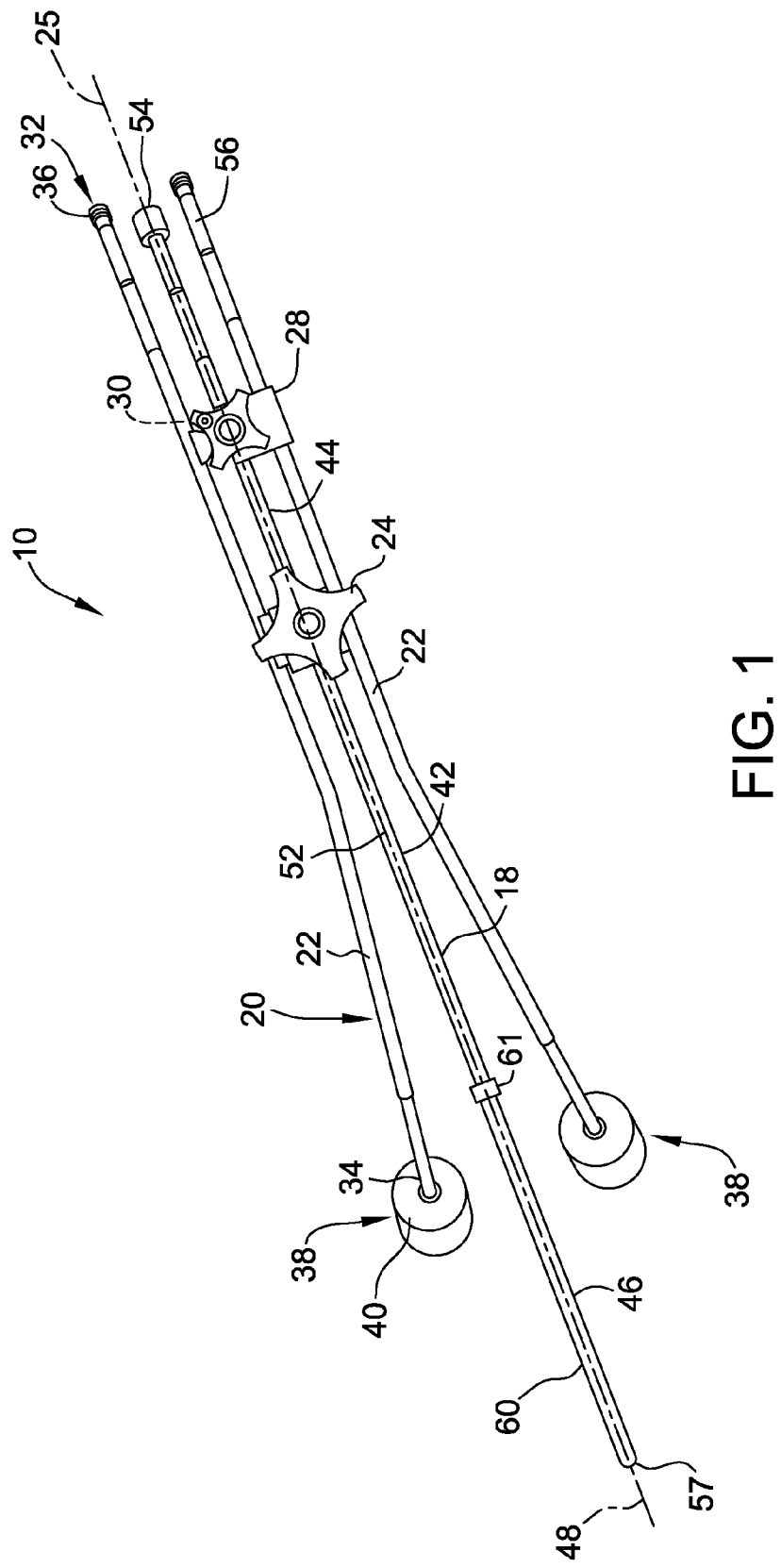
FIG. 1 is a perspective top view of an exemplary gynecological brachytherapy applicator.
Figure 2:
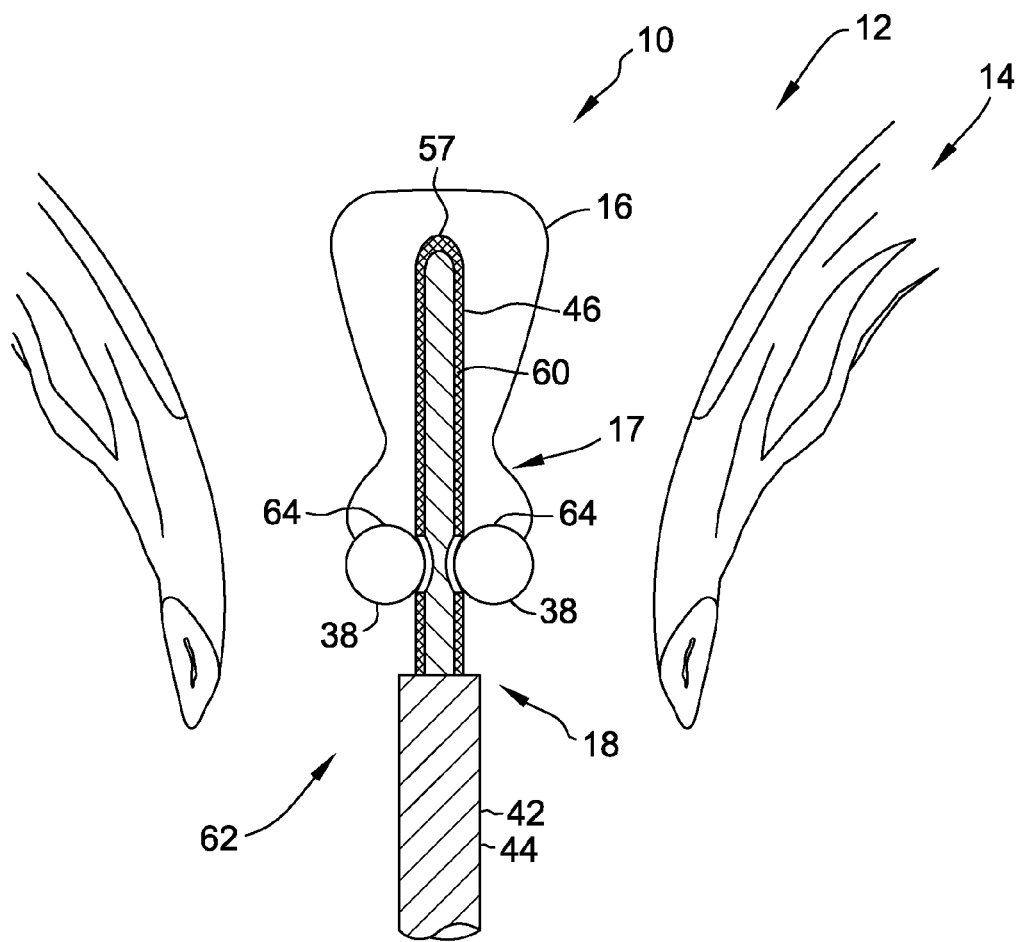
FIG. 2 is a coronal section of a portion of a female patient's anatomy including the exemplary gynecological brachytherapy applicator positioned within the uterus.
Figure 3:
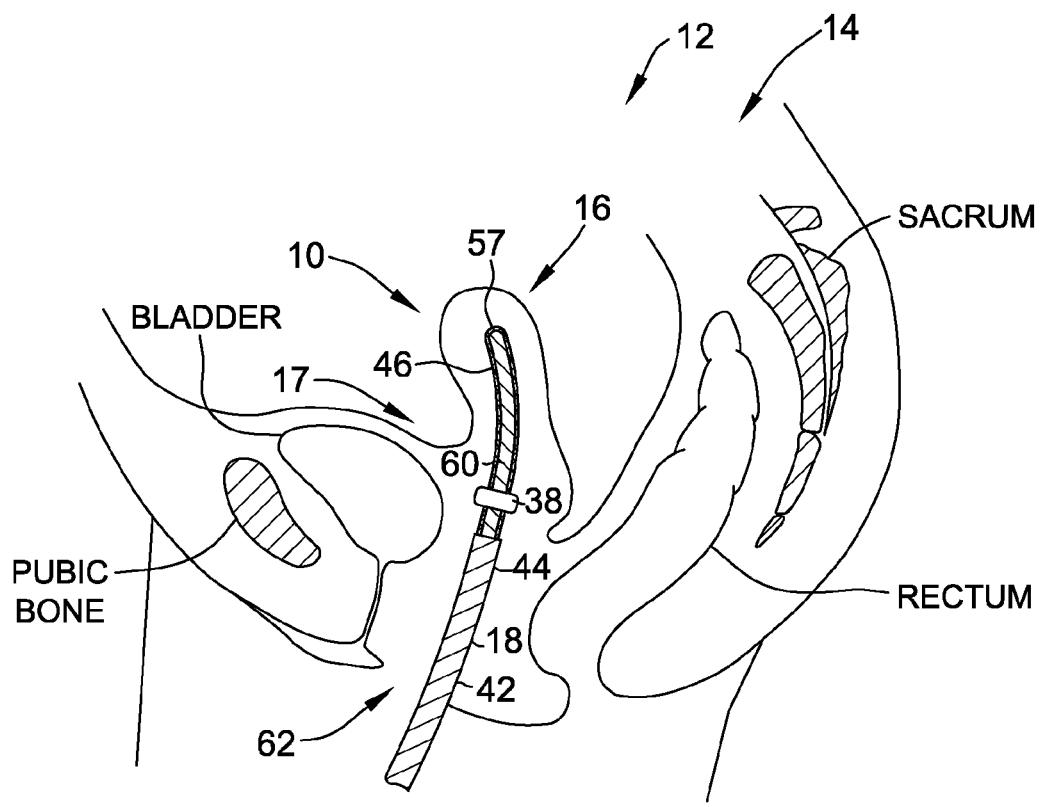
FIG. 3 is a medial sagittal section of a portion of the female patient's anatomy including the exemplary gynecological brachytherapy applicator positioned within the uterus.
Figure 4:
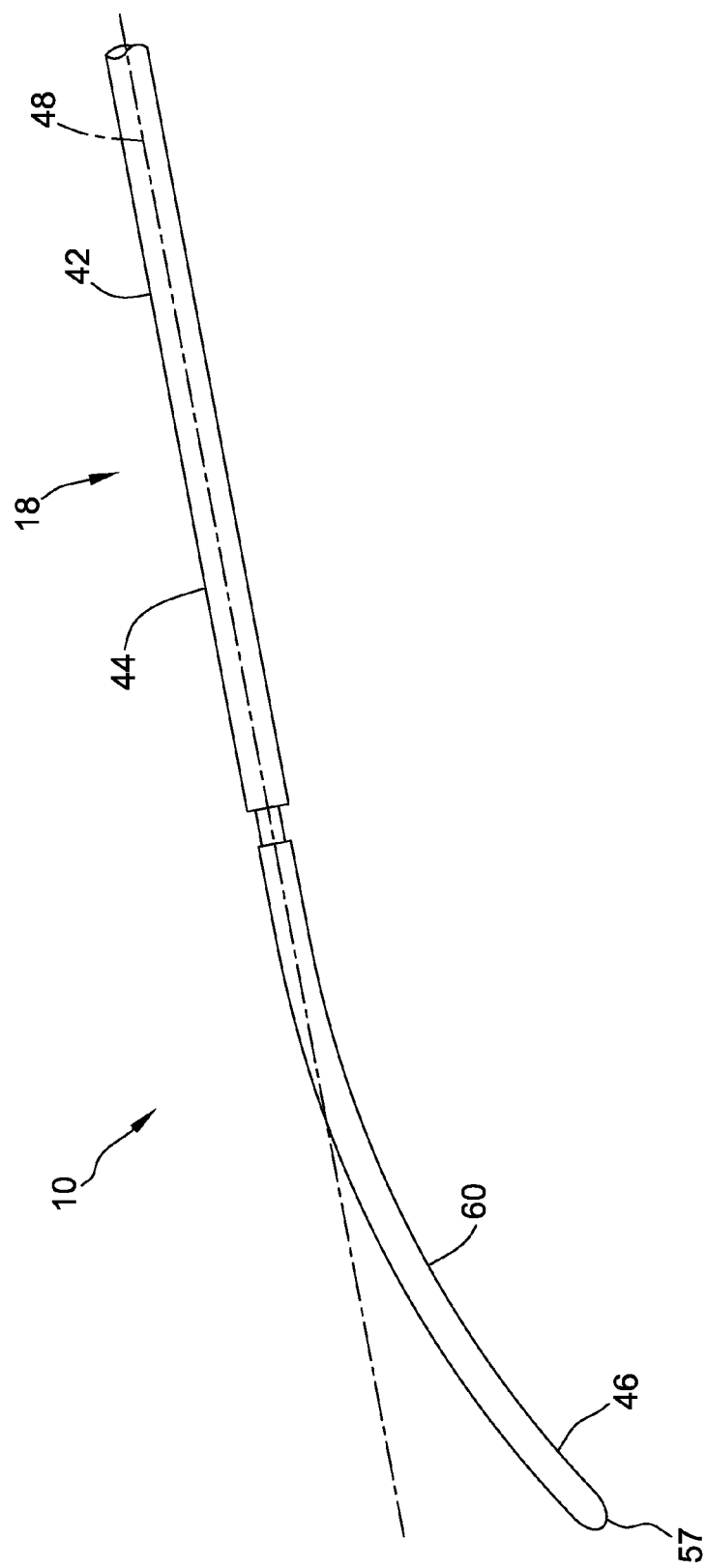
FIG. 4 is a perspective view of an exemplary tandem that may be used with the gynecological brachytherapy applicator shown in FIG. 1.

FIG. 1 is a perspective top view of a gynecological brachytherapy applicator 10. FIG. 2 is a coronal section of a portion of an anatomy 12 of a female patient 14 including gynecological brachytherapy applicator 10 positioned within uterus 16. FIG. 3 is a medial sagittal section of a portion of anatomy 12 of female patient 14 including gynecological brachytherapy applicator 10 positioned within uterus 16. FIG. 4 is a partial perspective view of gynecological brachytherapy applicator 10. In at least one embodiment, gynecological brachytherapy applicator 10 is a tandem and colpostat applicator that is configured to treat cervical and/or uterine cancer with high-dose-rate (HDR) brachytherapy. HDR includes delivering high-intensity radiation directly into tumor sites, wherein the tandem and colpostats are placed near a tumor formed adjacent to and/or including uterus 16 and/or a cervix 17 of patient 14, and radiation therapy is given through applicator 10 by selectively placing a radioactive source inside each hollow portion of applicator 10. However, it should be apparent to those skilled in the art and guided by the teachings herein that the embodiments described herein, may likewise be practiced in any suitable brachytherapy applications and is not limited to being practiced in only gynecological brachytherapy. For example, gynecological brachytherapy applicator 10 may include a ring and tandem applicator (shown in FIG. 8).

In at least one embodiment, applicator 10 includes an intrauterine tandem 18 and a pair 20 of colpostats 22. Each colpostat 22 is coupled to tandem 18 and oriented with respect to tandem 18 such that tandem 18 is positioned between colpostats 22. A pivot assembly 24 is coupled to each colpostat 22 and tandem 18. More specifically, tandem 18 is pivotably coupled to pivot assembly 24 to adjust an orientation of tandem 18 with respect to each colpostat 22. Moreover, pivot assembly 24 is slidably coupled to each colpostat 22 to adjust a position of tandem 18 along a longitudinal axis 26. A stop set screw 28 is coupled to each colpostat 22 to facilitate limiting a movement of each colpostat 22 such that each colpostat 22 is oriented a predefined width apart. Each colpostat 22 includes a radially inner surface 30 that defines a cavity 32 extending between a tip end 34 and a base end 36. Tip end 34 includes an ovoid 38, and a plastic cap 40 that is removably coupled to tip end 34. Tandem 18 and colpostats 22 are each formed from titanium. Alternatively, tandem 18 and/or colpostats 22 may include gold, a metal alloy, and/or any other suitable material that enables applicator 10 to function as described herein.

Tandem 18 includes a sidewall 42 that includes a base portion 44 and a tip portion 46. Base portion 44 extends along a centerline axis 48 of tandem 18. Tip portion 46 extends outwardly from base portion 44 and is oriented obliquely with respect to base portion 44. Sidewall 42 also includes a radially inner surface 50 (shown in FIG. 5), and a radially outer surface 52. Inner surface 50 defines a substantially cylindrical cavity 54 that extends between a first open end 56 and a second closed distal end 57. Base portion 44 extends between open end 56 and tip portion 46 and includes a length 58 (shown in FIG. 5) defined between open end 56 and tip portion 46 along axis 48. Tip portion 46 extends between base portion 44 and distal end 57, and include a length 59 (shown in FIG. 5) defined between base portion 44 and distal end 57. Tip portion 46 is configured to be inserted into uterus 16 such that distal end 57 extends into uterus 16 to facilitate delivering a radiation dose to a tumor affecting and/or involving uterus 16 and/or cervix 17.

Applicator 10 includes a sheath 60 (may also be referred to as a sleeve herein) that is removably coupled to tandem 18 to enhance an MR image of tandem 18 within patient 14 to enable the radiotherapy to be more optimally targeted to a tumor. Moreover, sheath 60 is configured to reduce metal artifacts in MR images of tandem 18 within patient 14 to facilitate improving visualization and localization of tandem 18 in the MR images during MR-guided intracavitary brachytherapy. In the exemplary embodiment, applicator 10 also includes an attachment assembly 61 that is coupled to sheath 60 and to tandem 18 to secure sheath 60 to tandem 18 to facilitate preventing a movement of sheath 60 with respect to tandem 18. In at least one embodiment, attachment assembly 61 is an o-ring. In another embodiment, attachment assembly 61 may be positioned near tip 46 of tandem 18 such that a narrowing of inner diameter 86 occurs. More specifically, attachment assembly 61 may couple to tip 46 of tandem 18 by narrowing diameter 86. Alternatively, attachment assembly 61 may be any suitable fastening device that enables applicator 10 to function as described herein.

During gynecological brachytherapy treatment, applicator 10 is inserted through a vagina 62 of patient 14 such that a high radiation dose may be delivered to the tumor involving uterus 16 and cervix 17. More specifically, applicator 10 is oriented such that tandem tip portion 46 is inserted into uterus 16, and ovoids 38 are positioned adjacent vaginal fornices 64 of patient 14. After insertion of applicator 10 within patient 14, MR imaging is used to display a position of tandem 18 and ovoids 38 with respect to the tumor affecting uterus 16 and cervix 17 within patient 14 to facilitate positioning of a radioactive source within tandem 18 and ovoids 38 to deliver a radiation dose to the tumor.

Figure 5:
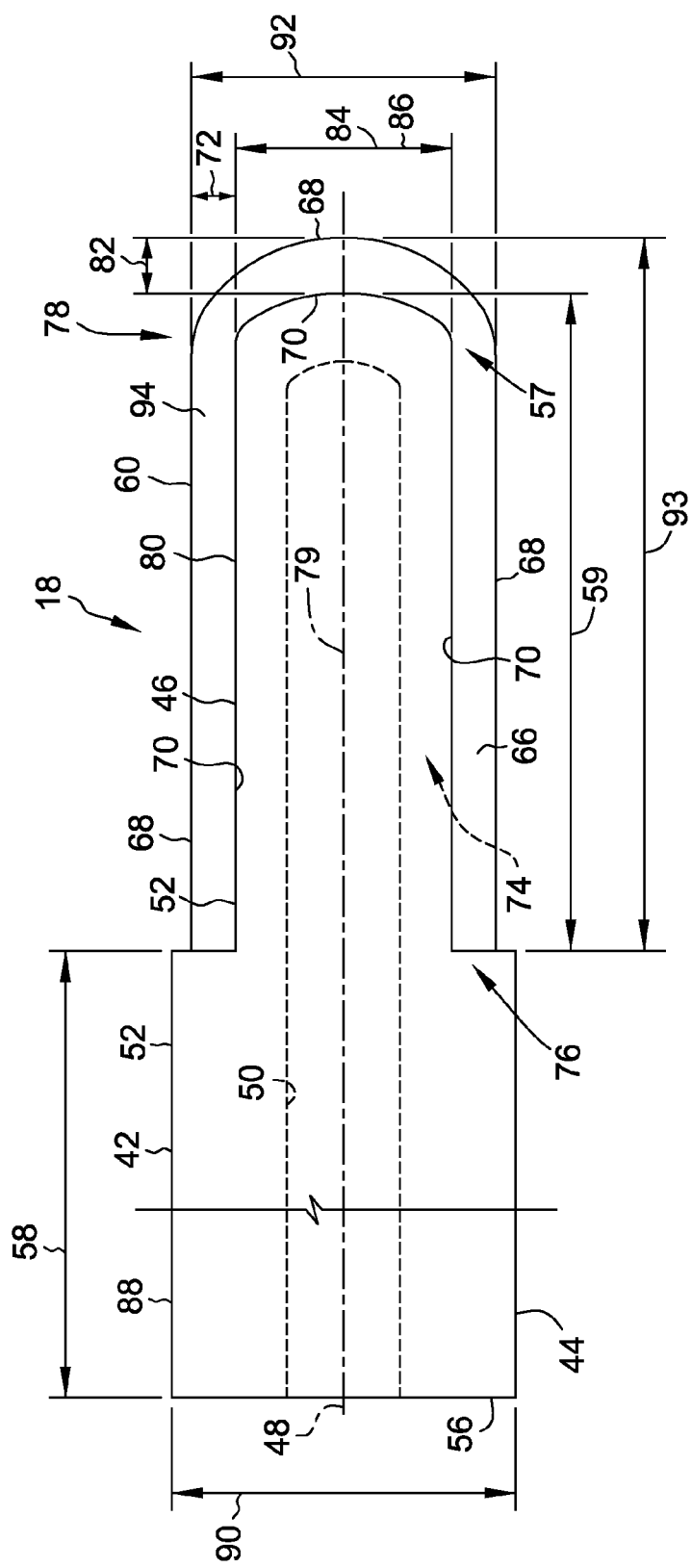
FIG. 5 is a partial sectional view of the tandem shown in FIG. 4.

FIG. 5 is a partial sectional view of the tandem 18. Identical components shown in FIG. 5 are labeled with the same reference numbers used in FIGS. 1-4. In at least one embodiment, sheath 60 includes a sidewall 66 that is adapted to be removably coupled to tip portion 46. Sidewall 66 extends between a radially outer surface 68 and a radially inner surface 70, and includes a thickness 72 measured between outer surface 68 and inner surface 70. In one embodiment, thickness 72 is between about 0.05 cm and about 0.15 cm. Alternatively, thickness 72 may be less than 0.05 cm, or greater than 0.15 cm. Inner surface 70 defines a cavity 74 that extends between a first open end 76 and a second closed end 78 along a centerline axis 79. Sheath cavity 74 is sized and shaped to receive tip portion 46 therein such that inner surface 70 substantially encapsulates tip portion 46. Moreover, tip portion 46 is oriented within sheath cavity 74 such that sheath inner surface 70 substantially circumscribes an outer surface 80 of tip portion 46, and such that sheath inner surface 70 is in contact with tip portion outer surface 80. Sheath 60 is adapted to be inserted into uterus 16 with tip portion 46, and to be removed from uterus 16 when tip portion 46 is removed from uterus 16. In addition, closed end 78 includes a thickness 82 measured between outer surface 68 and inner surface 70 along centerline axis 79. In one embodiment, closed end thickness 82 is between about 0.2 cm and about 0.5 cm. Alternatively, thickness 82 may be less than 0.2 cm, or greater than 0.5 cm.

In at least one embodiment, sheath inner surface 70 includes a first diameter 84 measured with respect to centerline axis 79. Tip portion outer surface 80 includes the second diameter 86 measured with respect to centerline axis 48. In one embodiment, tip portion diameter 86 is approximately equal to sheath inner surface diameter 84, such that said sheath inner surface 70 is in sealing contact with tip portion outer surface 80. Alternatively, sheath inner surface 70 may not be in sealing contact with tip portion outer surface 80. For example, in some embodiments, sheath 60 may include an air gap between end 57 of sheath 60 and tip 46 of tandem 18, and, as such, sheath inner surface 70 would not be in sealing contact with tip portion outer surface 80. In addition, base portion 44 includes an outer surface 88 that has a diameter 90 that is larger than tip portion diameter 86. Alternatively, tip portion diameter 86 may be approximately equal to, or larger than base portion diameter 90. Moreover, sheath outer surface 68 includes a diameter 92 that is less than base portion diameter 90. Alternatively, sheath outer surface diameter 92 may be approximately equal to, or larger than base portion diameter 90.

Sheath 60 also includes a length 93 measured between open end 76 and closed end 78. In at least one embodiment, sheath length 93 is approximately equal to tip portion length 59 such that sheath 60 extends across a full length 59 of tip portion 46. In another embodiment, sheath length 93 is less than tip portion length 59. Alternatively, sheath 60 includes a sheath length 93 that is greater than tip portion length 59, and is oriented such that sheath 60 extends across at least a portion of base portion outer surface 88.

In at least one embodiment, sheath 60 is formed from a plastic material 94 that is configured to reduce metal artifacts in MR images of tandem 18 within patient 14 and improve locating tip portion 46 with respect to a tumor involving uterus 16 and/or cervix 17 displayed in MR images. In one embodiment, sheath 60 includes polyethylene. Alternatively, sheath 60 may include any suitable material that enables applicator 10 to function as described herein.

Figure 20:
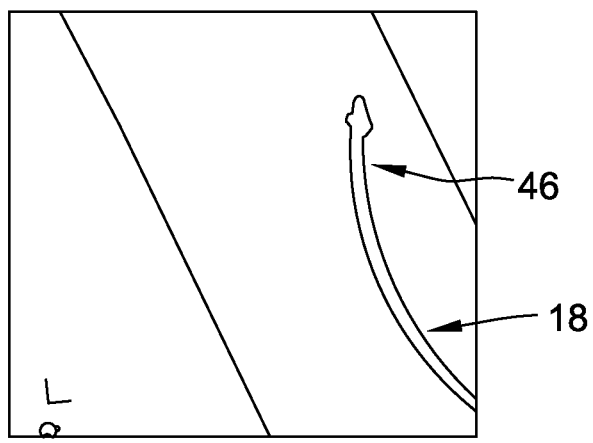
FIG. 20 is a schematic of an MR scan of an exemplary gynecological brachytherapy having a distorted tip.

In another embodiment, sheath 60 may be used to shift, if not completely mask, the distortion along the tandem 18 away from the tip of applicator 10 (shown in FIG. 20). More specifically, the tandem tip 46 may be displaced from the tip of sheath 60. Accordingly, the tip of sheath 60 is substantially distinct in an image and can be used to localize the tip of the applicator 10. In the exemplary embodiment, a relatively thicker plastic tip may be used to help shift the distortion away from the tip portion of the applicator. The thicker plastic tip may be used alone or in combination with an air gap between tip of sheath and tip of tandem to accomplish the shifting of the distortion in the image. In this embodiment, use of an air gap will prevent the inner surface of the sheath from being in sealing contact with the outer surface of the tandem.

Figure 6:
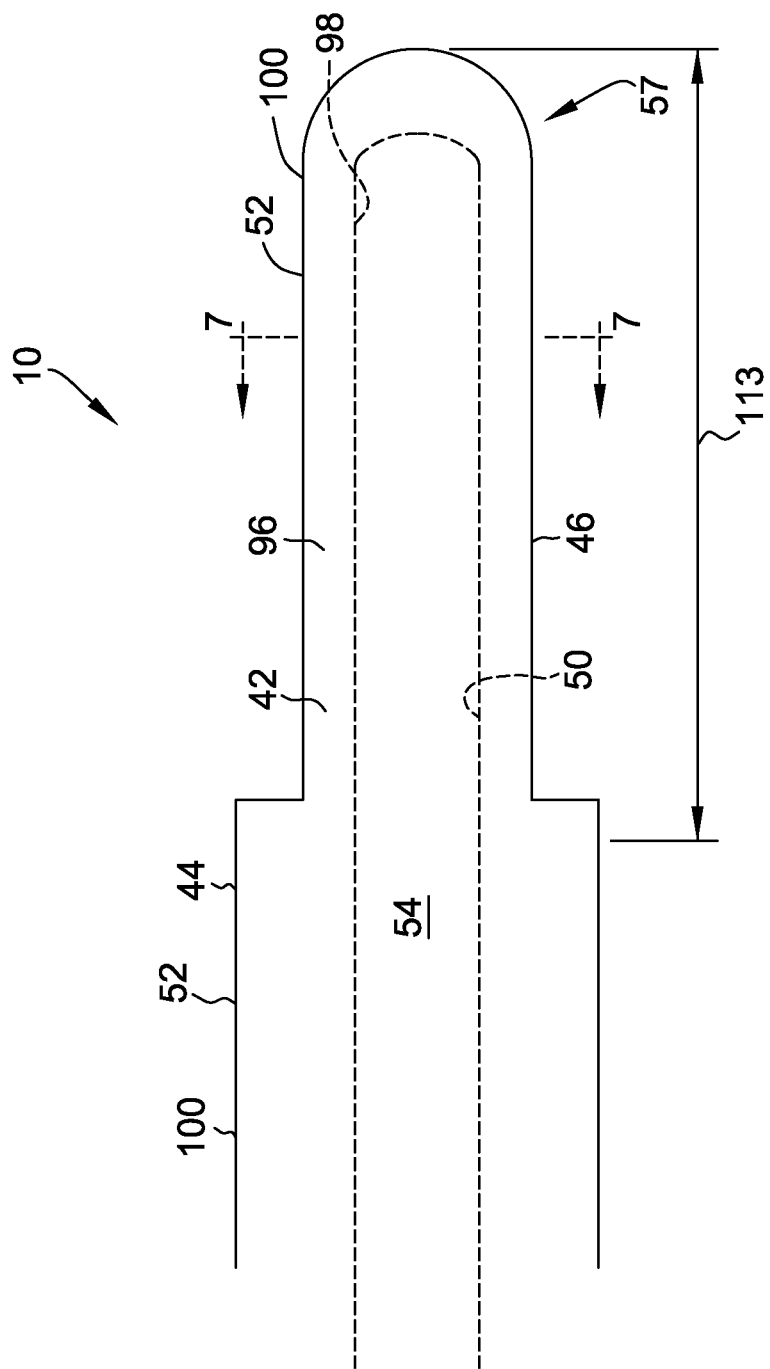
FIG. 6 is a partial sectional view of an alternative tandem that may be used with the gynecological brachytherapy applicator shown in FIG. 1.
Figure 7:
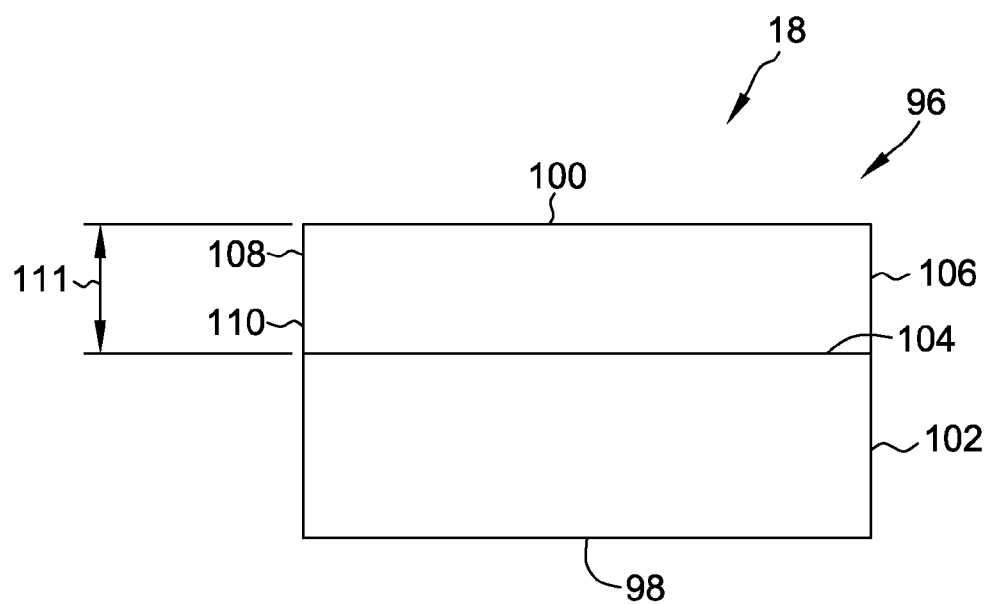
FIG. 7 is a cross-sectional view of the tandem shown in FIG. 6 and taken along line 7-7.

FIG. 6 is a partial sectional view of another embodiment of tandem 18. FIG. 7 is a cross-sectional view of tandem 18 and taken along line 7-7. Identical components shown in FIGS. 6-7 are labeled with the same reference numbers used in FIG. 5. In at least one embodiment, tandem 18 includes a sidewall 96 that extends between a radially inner surface 98 and a radially outer surface 100. Sidewall 96 includes a substrate material 102 that includes a surface region 104. Substrate material 102 is formed from titanium. Alternatively, substrate material 102 may include gold, a metal alloy, and/or any suitable material that enables applicator 10 to function as described herein.

Tandem 18 includes an imaging layer 106 that is deposited across at least a portion of surface region 104. Imaging layer 106 at least partially defines outer surface 100. In at least one embodiment, imaging layer 106 is deposited across at least a portion of tip portion 46, and is configured to reduce metal artifacts in MR images of tip portion 46 within patient 14 to facilitate improving visualization and localization of tip portion 46 in MR images of tandem 18 within patient 14 during MR-guided intracavitary brachytherapy. Imaging layer 106 includes at least one layer 108 that includes a plastic material 110. Alternatively, imaging layer 106 may include any suitable material that enables applicator 10 to function as described herein. In one embodiment, imaging layer 106 includes a thickness 111 that is between about 0.05 cm and about 0.5 cm. Alternatively, thickness may be less than 0.05 cm, or greater than 0.5 cm. In addition, imaging layer 106 may include a plurality of thicknesses along the length of tandem 18, wherein the cross-sectional thickness of tandem may vary across the full length of tandem, and at distal end 57.

In at least one embodiment, imaging layer 106 is deposited across tip portion 46 such that imaging layer 106 encapsulates distal end 57 and includes a length 113 measured from distal end 57 towards base portion 44 along axis 79. Alternatively, imaging layer 106 may extend from distal end 57 towards base portion 44 such that imaging layer 106 extends across a full length 59 of tip portion 46. In another embodiment, imaging layer extends from distal end 57 to base portion 44 such that imaging layer 106 is deposited across a full length 59 of tip portion 46 and at least a portion of base portion 44.

In at least one embodiment, substrate 102 includes a plastic material including a plurality of titanium fragments that are configured to increase a structural rigidity of the plastic material. The plastic material is configured to increase visualization and localization of tandem 18 in MR images of tandem 18 within patient 14.

Figure 8:
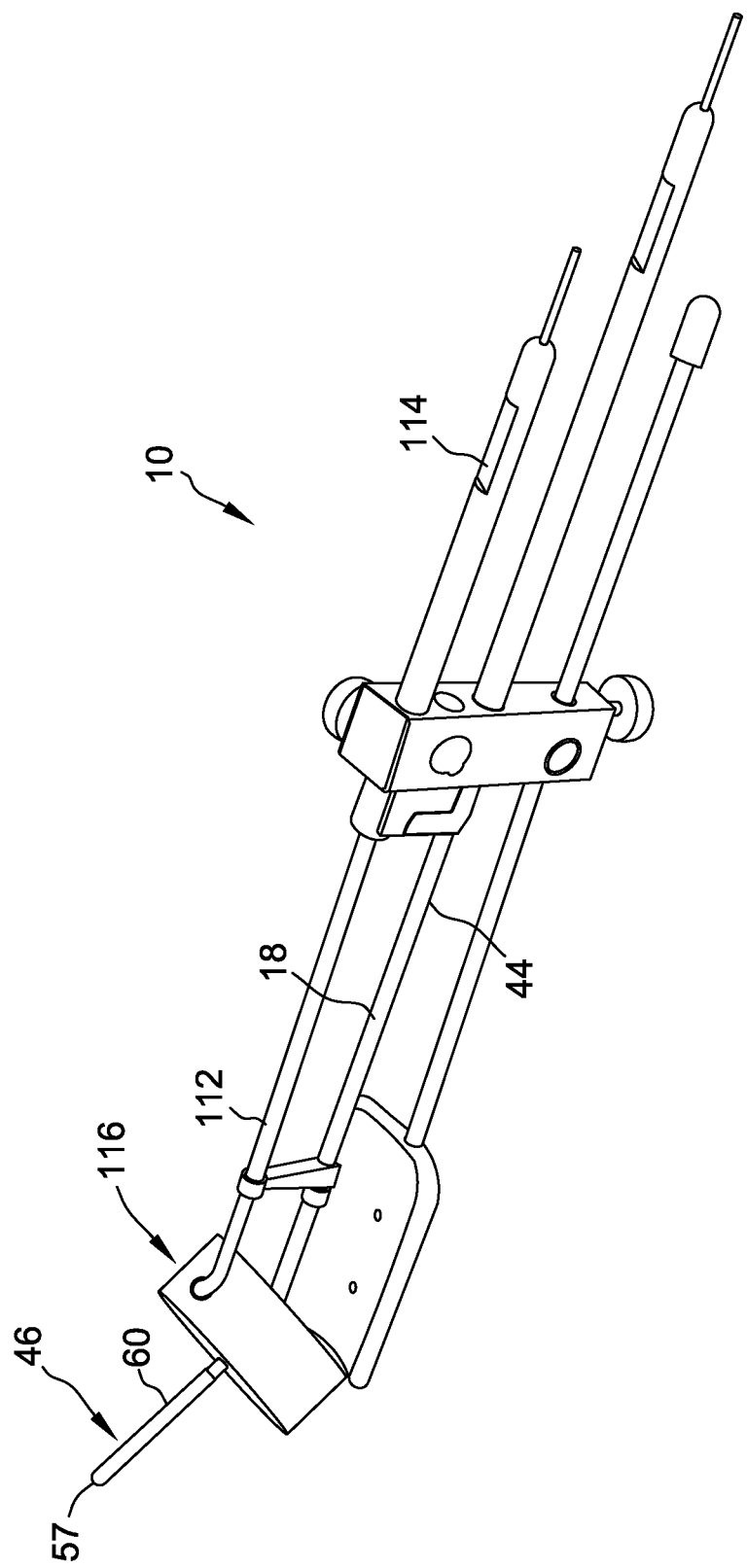
FIG. 8 is a schematic view of an alternative embodiment of the gynecological brachytherapy applicator shown in FIG. 1.
Figure 9:
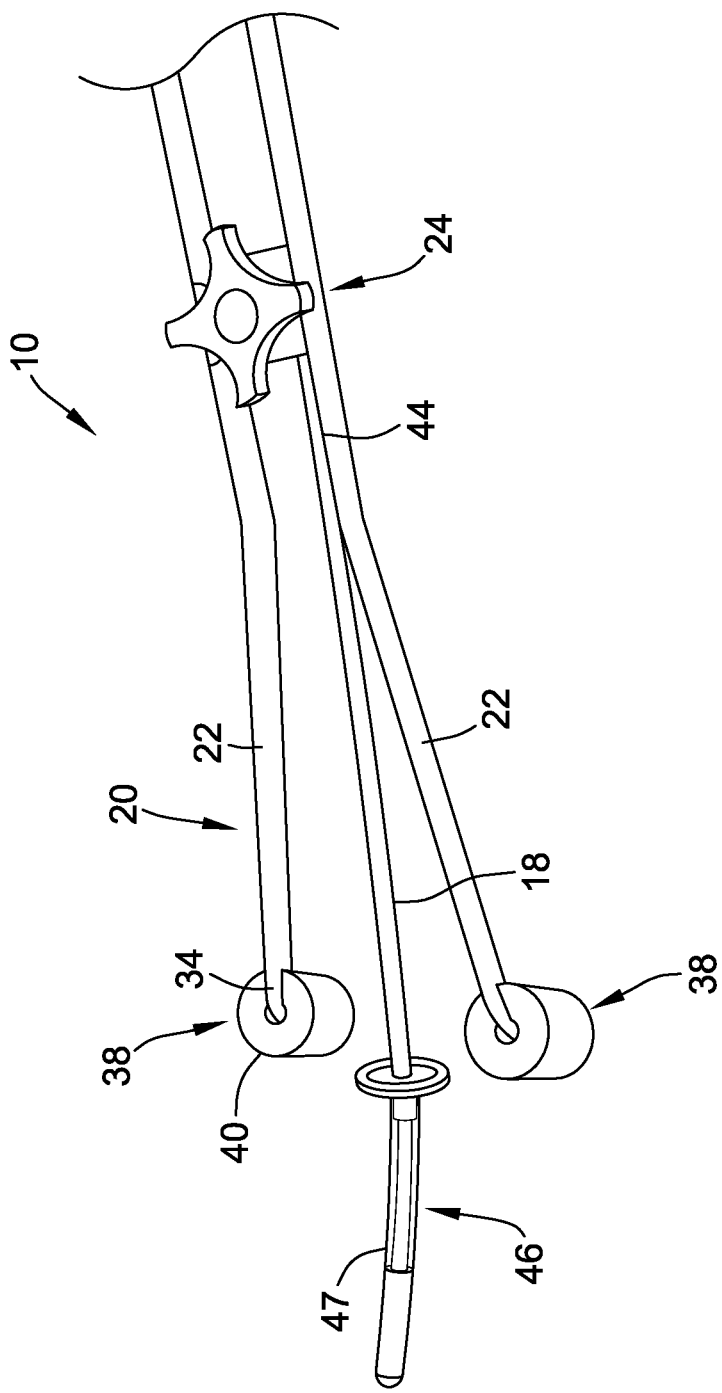
FIG. 9 is a schematic of a portion of an alternative embodiment of the gynecological brachytherapy applicator shown in FIG. 1 with a tandem and a sleeve.

FIG. 8 is a schematic view of another embodiment of gynecological brachytherapy applicator 10. Identical components shown in FIG. 8 are labeled with the same reference numbers used in FIG. 1. In at least one embodiment, applicator 10 includes a ring applicator 112 that is coupled to tandem 18. Ring applicator 112 includes a handle portion 114 and a ring portion 116 extending outwardly from handle portion 114. Tandem 18 is oriented with respect to ring applicator 112 such that tip portion 46 extends through ring portion 116. During gynecological brachytherapy treatment, applicator 10 is positioned within patient 14 such that tip portion 46 is inserted into uterus 16, and ring portion 116 is positioned adjacent to vaginal fornices 64.

The embodiments of the applicator and method for using the applicator, as described herein, were tested in the following exemplary experiment.

EXPERIMENT

Figure 10:
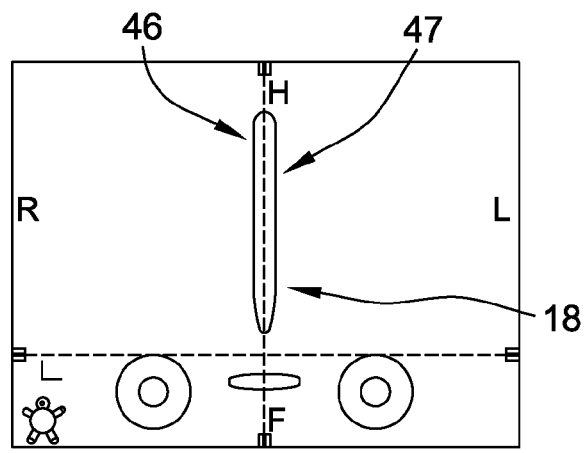
FIG. 10 is a schematic of a CT scan of a top view of the gynecological brachytherapy applicator with the tandem and the sleeve shown in FIG. 9.
Figure 11:
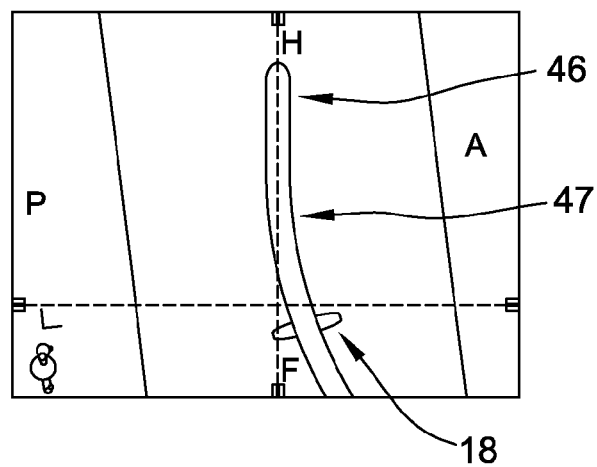
FIG. 11 is a schematic of a CT scan of a side view of the gynecological brachytherapy applicator with the tandem and the sleeve shown in FIG. 9.
Figure 12:
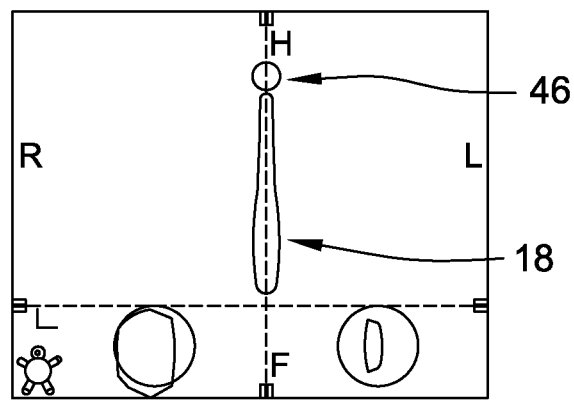
FIG. 12 is a schematic of a proton density weighted (PDW) MRI scan of a top view of an exemplary gynecological brachytherapy applicator with a 2.5 mm slice.
Figure 13:
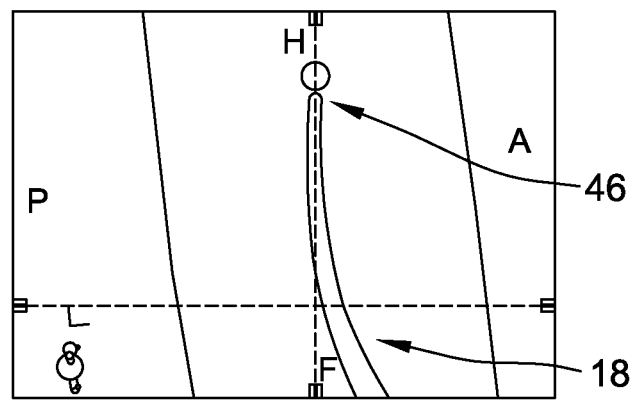
FIG. 13 is a schematic of a PDW MRI scan of a side view of the gynecological brachytherapy applicator shown in FIG. 12.
Figure 14:
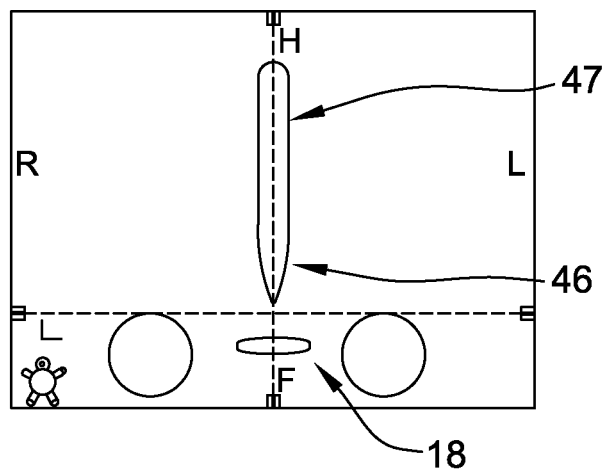
FIG. 14 is a schematic of a PDW MRI scan of a top view of an exemplary gynecological brachytherapy applicator with a 2.5 mm slice and having a sleeve.
Figure 15:
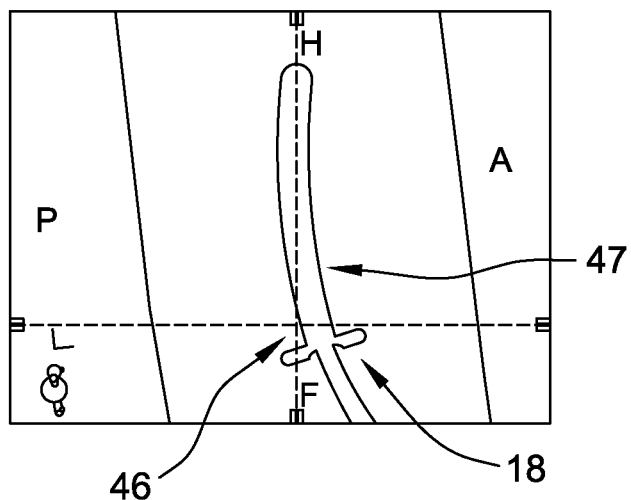
FIG. 15 is a schematic of a PDW MRI scan of a side view of the gynecological brachytherapy applicator with the sleeve shown in FIG. 14.
Figure 16:
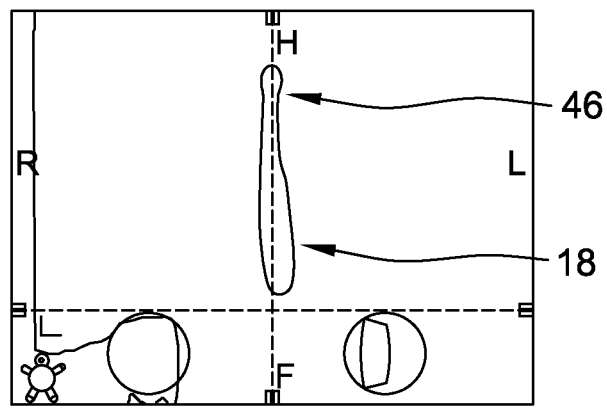
FIG. 16 is a schematic of a PDW MRI scan of a top view of an exemplary gynecological brachytherapy applicator with a 2.5 mm slice and a readout direction swapped from anterior-posterior (AP) to foot-head (FH).
Figure 17:
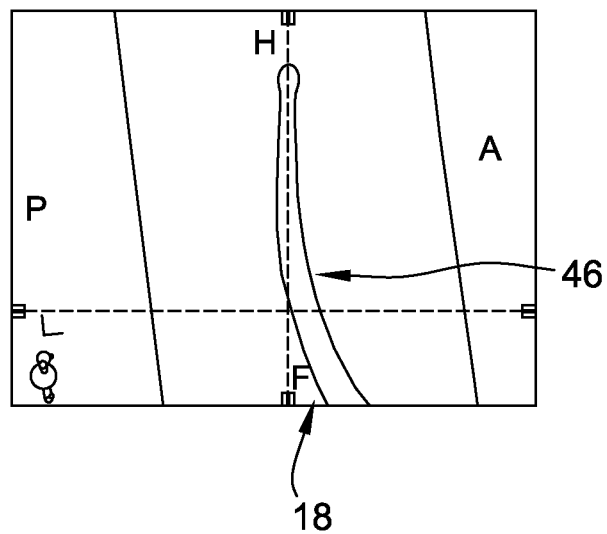
FIG. 17 is a schematic of a PDW MRI scan of a side view of the gynecological brachytherapy application shown in FIG. 16.
Figure 18:
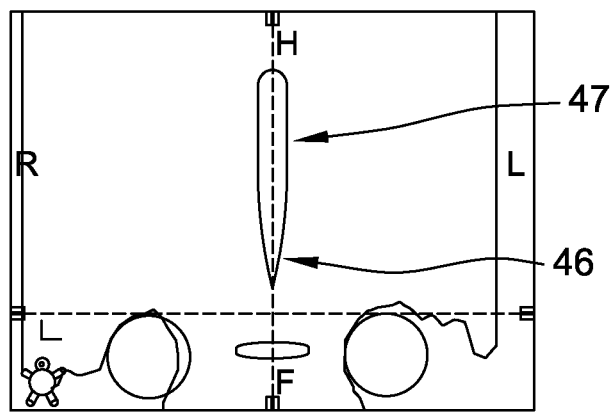
FIG. 18 is a schematic of a PDW MRI scan of a top view of an exemplary gynecological brachytherapy applicator with a 2.5 mm slice, with a sleeve, and with a readout direction swapped from AP to FH.
Figure 19:
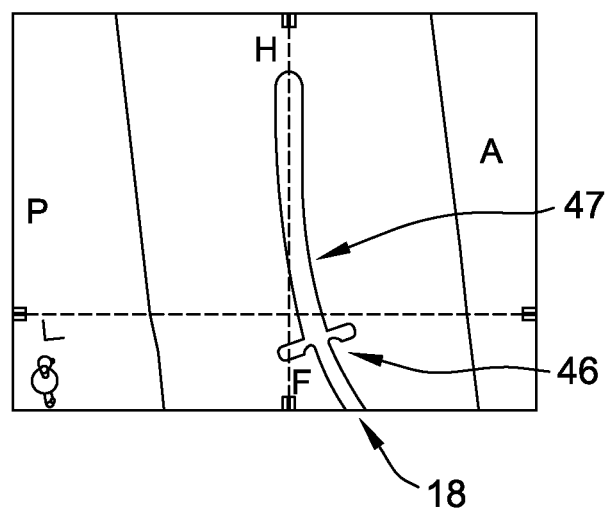
FIG. 19 is a schematic of a PDW MRI scan of a side view of the gynecological brachytherapy applicator with the sleeve shown in FIG. 18.

During imaging of the gynecological brachytherapy applicator, a titanium tandem and colpostat applicator was fitted with a plastic sheath. The applicator was fixed rigidly within a plastic phantom containing copper sulfate solution, and then imaged on a multi-slice CT scanner to obtain a reference image dataset (shown in FIGS. 10-11) and subsequently on a 1.5 T MR scanner to obtain nine test image datasets acquired using different MR sequences (T2-weighted, T1-weighted, and proton-density-weighted with turbo-spin-echo technique), slice thicknesses (0.5 cm and 0.25 cm in the parasagittal plane), and fold-over directions (anterior-posterior "AP" versus foot-head "FH") (PDW images shown in FIGS. 12-19). Imaging was then repeated with cervical stent removed, yielding two MR image datasets for comparison, "stented" (with a sleeve or sheath) and "non-stented" (without a sleeve or sheath). All images were imported into a brachytherapy treatment planning system, fused to CT, and planned for delivery of an HDR treatment with a 0.5 cm Ir-192 source using our standard treatment protocols. Two measures were used to assess the geometric distortion of the tandem on the MR images. Differences in the 3D coordinates of the distal most dwell position in the tandem on the CT were compared against those on the registered MR datasets in terms of differences in right-left (RL), FH, and AP directions. Also, intensity profiles of the tandem were measured in the parasagittal plane near the tip of the tandem and at another position approximately 1.5 cm inferior along the tandem. The diameter of the tandem was derived from each resulting profile and compared to the known diameter (with or without stent).

The mean differences in the RL and AP coordinates of the distal most dwell position were less than 0.1 cm for both stented and non-stented scans; however, addition of the stent decreased the mean differences in the FH coordinate from 0.20±0.08 cm to 0.02±0.07 cm. Mean differences in tandem diameter on the non-stented images were 0.17±0.08 cm near the tip and 0.11±0.03 cm at 1.5 cm inferior to the tip. Addition of the stent reduced these mean differences in diameter to 0.01±0.03 cm and 0.02±0.04 cm, respectively. As such the use of a plastic sheath or sleeve on a titanium tandem reduces metal artifacts in MR images. Thus, the use of a plastic sheath or coating on the tandem improves tandem visualization and localization for MR-guided intracavitary brachytherapy planning.

Exemplary embodiments of a gynecological brachytherapy applicator for use in MR-Guided intracavitary brachytherapy are described above in detail. The systems and methods are not limited to the specific embodiments described herein, but rather, components of the systems may be utilized independently and separately from other components described herein. For example, the components may also be used in combination with other brachytherapy systems, and are not limited to practice with only the system as described herein. Rather, the exemplary embodiments can be implemented and utilized in connection with many other brachytherapy applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A gynecological brachytherapy applicator for use in delivering a radiation dose to a tumor affecting at least one of a uterus and a cervix of a patient, said applicator comprising:
   an intrauterine tandem comprising a base portion and a tip portion extending outwardly from said base portion, said tip portion configured to be inserted within the uterus to facilitate delivering a radiation dose to an area including the uterus and the cervix; and
   a sheath removably coupled to said tandem, said sheath comprising an inner surface that defines a cavity extending between a first open end and a second closed end, said tip portion oriented within said cavity such that said sheath inner surface substantially circumscribes an outer surface of said tip portion and wherein said tip portion outer surface has a first diameter and said sheath inner surface has a second diameter that is approximately equal to said first diameter such that said sheath inner surface is in sealing contact with said tip portion outer surface, said sheath comprising a plastic material.

2. A gynecological brachytherapy applicator in accordance with claim 1, further comprising a pair of colpostats coupled to said tandem, each of said colpostat comprising an inner surface that defines a cavity extending between a tip end and a base end, and a plastic cap removably coupled to said tip end.

3. A gynecological brachytherapy applicator in accordance with claim 1, further comprising a ring applicator coupled to said tandem, said ring applicator comprising a handle portion and a ring portion extending outwardly from said handle portion, said tandem oriented with respect to said ring applicator such that said tandem tip portion extends through said ring portion.

4. A sheath for use with a gynecological brachytherapy applicator, the applicator including an intrauterine tandem that includes a base portion and a tandem tip portion extending outwardly from the base portion, said sheath comprising a sidewall comprising an inner surface that defines a cavity extending between a first open end and a second closed end, said cavity sized to receive the tandem tip portion therein such that said inner surface substantially encapsulates the tip tandem portion and such that said inner surface is in sealing contact with the tip tandem portion outer surface, said sheath adapted to be removably coupled to the tandem tip portion.

5. A sheath in accordance with claim 4, wherein said sheath comprises polyethylene.

6. A gynecological brachytherapy applicator for use in delivering a radiation dose to a tumor affecting at least one of a uterus and a cervix of a patient, said applicator comprising:
an intrauterine tandem comprising a base portion and a tip portion extending outwardly from the base portion, said tip portion configured to be inserted within the uterus to facilitate delivering a radiation dose to an area including the uterus and the cervix, said tandem further comprising a sidewall extending between a radially inner surface and a radially outer surface, said sidewall comprising:
a substrate material comprising a surface region; and
at least one imaging layer deposited across said surface region to at least partially define said tip portion outer surface.

7. A gynecological brachytherapy applicator in accordance with claim 6, wherein said substrate material is formed from a metal alloy.

8. A gynecological brachytherapy applicator in accordance with claim 6, wherein said substrate material is formed from at least one of titanium and gold.

9. A gynecological brachytherapy applicator in accordance with claim 6, wherein said tandem further comprises a substantially cylindrical cavity that is defined by said tip portion inner surface, said cylindrical cavity extends between an open end and a closed end.

10. A gynecological brachytherapy applicator in accordance with claim 9, wherein said tip portion extends between said base portion and said closed end, and wherein said tip portion includes a length defined between said base portion and said closed end.

11. A gynecological brachytherapy applicator in accordance with claim 10, wherein said base portion includes a length defined between said open end and said tip portion along a centerline axis of said tandem.

12. A gynecological brachytherapy applicator in accordance with claim 9, wherein said base portion extends between said open end and said tip portion.

13. A method of using a gynecological brachytherapy applicator for delivering a radiation dose to a tumor affecting a uterus and a cervix of a patient, said method comprising:
coupling a removable sheath to an intrauterine tandem that includes a base portion and a tip portion that extends outwardly from the base portion, wherein the sheath includes an inner surface that defines a cavity extending between an open end and a closed end, the sheath further includes a plastic material, and wherein the tip portion includes an outer surface having a first diameter and the sheath inner surface has a second diameter that is approximately equal to the first diameter;
orienting the tip portion within the cavity such that the sheath inner surface substantially circumscribes the outer surface of the tip portion and such that the inner surface is in sealing contact with the tip tandem portion outer surface;
inserting the tandem through a vagina of the patient such that the tip portion is at least partially within the uterus; and
delivering a radiation dose to the uterus and the cervix.

14. A method in accordance with claim 13, further comprising coupling a pair of colpostats to the tandem, wherein each of the colpostats includes an inner surface that defines a cavity extending between a tip end and a base end.

15. A method in accordance with claim 14, further comprising coupling a removable plastic cap to the tip end.

16. A method in accordance with claim 13, further comprising coupling a ring applicator to the tandem, wherein the ring applicator includes a handle portion and a ring portion extending outwardly from the handle portion.

17. A method in accordance with claim 16, further comprising orienting the tandem with respect to the ring applicator such that the tandem tip portion extends through the ring portion.

* * * * *